United States Patent [19]

Manning et al.

[11] Patent Number: 4,645,666

[45] Date of Patent: Feb. 24, 1987

[54] VACCINE FOR BLUETONGUE DISEASE EMPLOYING PLATINUM COMPOUNDS

[75] Inventors: Jarue S. Manning, Davis, Calif.; Giorgio Poli, Milan, Italy

[73] Assignee: The Regents of the University of California, Berkeley, Calif.

[21] Appl. No.: 386,469

[22] Filed: Jun. 8, 1982

[51] Int. Cl.[4] .......................... A61K 39/12; C12N 7/06
[52] U.S. Cl. ........................................ 424/89; 435/238
[58] Field of Search ................... 424/89, 131; 435/238

[56] References Cited

U.S. PATENT DOCUMENTS

| | | | |
|---|---|---|---|
| 3,847,737 | 11/1974 | Kanarek | 435/238 |
| 4,053,587 | 10/1977 | Davidson et al. | 424/131 |
| 4,273,755 | 6/1981 | Rhoda et al. | 423/463 |
| 4,344,935 | 8/1982 | Leclerc et al. | 424/89 |
| 4,370,264 | 1/1983 | Kotitschke et al. | 260/112 B |

FOREIGN PATENT DOCUMENTS 1585203  2/1981  United Kingdom ................ 424/131

OTHER PUBLICATIONS

Kemeny et al., Am. J. Vet. Res., 22: 921–925 (1961).
Parker et al., Vet. Rec., 96: 284–287 (1975).
Davis et al., Microbiology, Harper and Row, New York, 1973, pp. 1463–1464.
Kutinova et al., Neoplasma (1972) 19: 5.
Davis, Bernard D., and others, *Microbiology: Including Immunology and Molecular Genetics*, Philadelphia: Harper & Row, 1980, pp. 855 & 1273.

*Primary Examiner*—Sam Rosen
*Assistant Examiner*—Shawn P. Foley
*Attorney, Agent, or Firm*—Bertram I. Rowland

[57] ABSTRACT

Vaccine prepared by inactivation of non-enveloped virus with cis-diamino chelated platinous halide in presence of an effective amount of a detergent. Method of inactivation particularly applicable employing a non-ionic detergent in inactivating a double stranded RNA virus.

17 Claims, No Drawings

VACCINE FOR BLUETONGUE DISEASE EMPLOYING PLATINUM COMPOUNDS

This invention was made with Government support under Cooperative Agreement 58-9 AHZ-9-448 with the U.S. Department of Agriculture. The Government has certain rights in this invention.

BACKGROUND OF THE INVENTION

1. Field of the Invention

The use of attenuated or killed pathogens has become a classical technique in vaccination to protect a mammalian host from a pathogen. However, the use of intact organisms has many concerns. It is not sufficient that there be a high rate of kill of the viable organism. Unless one can be assured that there is complete mortality or attenuation, the vaccine becomes the infective agent. Furthermore, where the genome of the organism is retained, there is the further concern that potential complementation can result in a genome which will be capable of replication and become infectious.

Besides the safety concerns, there is also the question of whether the attenuated or killed pathogen will serve as an effective immunogen. Where the lifetime of the modified pathogen in the host is unreasonably short, it may not provide a sufficient period of exposure to develop a strong immunogenic response. Also, the method of attenuating or killing the pathogen may result in conformational modifications of the pathogen. The immunogenic response may therefore be to determinants other than the wild type pathogen.

Finally, there is the concern that the modifying agent, where a chemical reagent is used, must not be detrimental to the host on administration to the host. Therefore, any agent which is used must either be removed prior to administration to the host or alternatively should have little if any detrimental effect on the host.

In view of the numerous constraints on preparing attenuated or killed vaccines, only a few pathogens have been modified and shown to be effective vaccines.

2. Description of the Prior Art

Kutinova et al., Neoplasma (1972) 19:5 describes the inactivation of papovavirus. SV40 by cis-dichlorodiammine platinum (II). Roberts and Thomson, Progress in Nucleic Research and Molecular Biology (1979) 22:71 describe the mechanism of action of antitumor platinum compounds. See also the references cited therein.

SUMMARY OF THE INVENTION

Methods and compositions are provided for preparing a vaccine for use in protecting a host against a non-enveloped virus. Particularly, non-enveloped viruses having double stranded nucleic acids in their genome are treated in the presence of a detergent with a cis-platinous halide complex, substantially non-toxic to said host, in an amount sufficient to provide mortality of said virus to provide a safe vaccine. The resulting killed virus may then be formulated in conventional ways for vaccination of a host.

DESCRIPTION OF THE SPECIFIC EMBODIMENTS

Methods and compositions are provided for preparing vaccines by killing viruses to provide a vaccine product which is safe, while retaining the immunogenicity of the original virus. By contacting a virus with a chelated platinous halide in the presence of a minor amount of a detergent, the virus is completely inactivated resulting in a product which may be formulated and safely administered to a mammalian host.

The viruses are initially grown to a sufficient concentration in host cells. The viruses which are employed in the subject invention are non-enveloped viruses, in that upon lysis of the invaded cell, the virus is not encapsulated in the host cell's membrane on release. A wide variety of viruses are non-enveloped which attack mammalian hosts. Hosts for which vaccines are of interest include humans, domestic animals, such as ovine, porcine, canine, equine, bovine, etc., laboratory animals, such as primates, lagomorpha, rodentia, as well as the class Aves.

The viruses are characterized by being non-enveloped, usually having a double stranded genome, more particularly double stranded RNA. In addition, the viruses are sensitive to treatment with platinous halide compounds. While it is believed that the platinous halides serve to cross link nucleic acid strands, it is not intended to be limited to this mechanism of inactivation. Illustrative of various classes of viruses which may be inactivated in accordance with the subject invention are orbivirus, rotavirus, picornaviruses, reoviruses, rhinoviruses, coxsackievirus, etc. Particular viruses include bluetongue virus (BTV) reovirus type 3, polio virus, Rous sarcoma virus.

In order to prepare the vaccine, it is desirable to grow host cells to a sufficient concentration, followed by inoculation with the virus. Conveniently, the viruses are grown in conventional cellular cultures in an appropriate nutrient medium, supplemented with appropriate amino acids, serum, antibiotics and buffer. The cells are infected with from about 0.001 to about 2 plaque-forming units (PFU) per cell and incubated for from about 12 to 48 hrs. The incubation is terminated and the virus harvested from the viral infected cells when about 90% or more of the cells show cytopathic effects of infection.

The virus is then isolated by conventional techniques. Conveniently, the host cells may be washed and pelleted, followed by resuspension of the pelleted cells in an appropriately buffered medium, generally at a pH of about 7 to 8.

In order to release the virus from the cells, the cells are disrupted by any convenient means. Sonication, mechanical grinding, osmolysis, and the like, may be employed. The virus may then be freed of the cellular debris by any convenient means, the means depending upon the manner in which the cells were lysed.

Where the cells were sonicated, the sonicated solution may be centrifuged for a sufficient time to pellet the nuclei and other large material. If desired, further purification can be carried out, employing ultrafiltration, density gradient centrifugation, or the like. It is normally not necessary to extensively purify the virions, although it is found that the presence of cellular debris may require an increased concentration of the platinous halide salt. Thus, a relatively crude purification of the virions is sufficient, although in some instances further purification may be desirable.

Once the virions have been isolated, they may then be used for inactivation. The inactivation is carried out by contacting them with a mild detergent and a platinous halide salt, either concurrently or consecutively, preferably consecutively.

The virion particles are employed dispersed in an aqueous medium, conveniently the same buffered medium in which the cells were lysed. The pH will normally be about 6.5 to 7.5 and any convenient buffer may be employed, conveniently phosphate buffer. The detergent is added in small amounts generally at least about 0.001, more usually at least about 0.05 weight percent and not more than about 0.75 weight percent, preferably not more than about 0.3 weight.

Various detergents may be used, particularly nonionic detergents. These detergents are normally polymers of ethylene oxide or propylene oxide or combinations thereof, generally of at least about 1,000 molecular weight and usually not exceeding 100,000 molecular weight, more usually from about 1,000 to 50,000 molecular weight. The detergents are water soluble at the concentrations used and may have one or both of the terminal hydroxyl groups modified by etherification or esterification with aliphatic or aromatic groups, generally ranging from about 1 to 20 carbon atoms, more usually ranging from about 4 to 18 carbon atoms. The terminal groups will usually have only carbon, hydrogen and oxygen, where the oxygen is present as hydroxyl or ether.

A wide variety of nonionic detergents are sold under a variety of names, such as Tween QS, PEG, etc. the Triton series being of particular interest.

Conveniently, the nonionic detergent is added to the desired concentration to the buffered solution containing the virion particles and the mixture allowed to stand for a short period of time, normally greater than about 5 minutes and not more than about 30 minutes. While longer times may be employed, no significant advantage is observed for the extended period.

The platinous halide salt inactivant is then added to at least an inactivating concentration, conveniently in the presence of the nonionic detergent. The platinous halide salt will be a cis-chelate, particularly a diamino chelate. While ammonia or various substituted amines may be employed, normally having alkyl groups of from about 1 to 3 carbon atoms, for the most part, there is no advantage in the presence of the alkyl substituents. Therefore, the unsubstituted ammonia will be employed as the chelating agent.

As previously indicated, the amount of the inactivant will vary depending upon the purity of the virion composition. With a highly purified virion composition, concentrations as low as 1 $\mu$g/ml may be employed, although usually at least about 2 $\mu$g/ml will be employed. Usually, the total amount of inactivant will not exceed 200 $\mu$g, more usually not exceeding about 125 $\mu$g. The virion concentration will generally be from about $10^5$ to $10^9$ pfu/ml, more usually from about $10^6$ to $10^8$ pfu/ml. The time will be sufficient to ensure the complete inactivation of the virions. For the most part, the incubation period will be at least about 30 minutes, and will usually require not more than about 180 minutes, usually requiring not more than about 120 minutes. Mild temperatures are sufficient, generally ranging from about 10° to 40° C., and conveniently, ambient temperatures may be employed. Desirably, the mixture may be mildly agitated to prevent settling or localized concentration.

The inactivation solution may then be used as a vaccine or may be further modified. The virions may be crosslinked with conventional crosslinking agents which will be acceptable to the host, such as dimethyl superimidate, glutaraldehyde, etc. Depending upon the inactivant concentration, the inactivation medium may be diluted 10 to 1000 fold before use. At concentrations of about 50 to 200 $\mu$g/ml dilution will usually be about 10 to 100. Desirably, the vaccine may be combined with an adjuvant to enhance the immune response. Various adjuvants may be employed, such as incomplete Freund's adjuvant (Difco); a peanut oil, glycerol, lecithin adjuvant; aluminum hydroxide; or the like. Any convenient adjuvant may be employed, which is acceptable to the host, and enhances the immune response.

The vaccine may be applied to the host in any convenient way, particularly parenterally, more particularly by injection, for example, intramuscularly, intraperitoneally, subcutaneously, or the like. Usually, a convenient dosage is about 1 to 2 ml. One or more booster injections may be employed at from about 2 to 6 week intervals. The blood of the host may be monitored for production of antibodies to the virion.

The following examples are given by way of illustration and not by way of limitation.

EXPERIMENTAL

Bluetongue virus (BTV) infected cells are harvested when 90% or more of cells are showing cytopathic effects of infection. The cells are washed and pelleted. Pelleted cells are resuspended in standard phosphate buffer adjusted to pH 7.2. The resuspended cells are then sonicated to disrupt the cells and release the virus. The sonicated solution is then centrifuged at 10,000xg for 20 minutes to pellet nuclei and other large material. The supernatant fluid is then adjusted to 0.1% Triton X-100 and the fluid allowed to stand at room temperature for 15 minutes. The inactivant, diammine dichloro-cis-platinum(II) prepared in phosphate buffer, pH 7.2, is added to yield a final concentration of 100 $\mu$g inactivant per ml of fluid. The drug-treated sample is allowed to stand at room temperature for 90 minutes with occasional mild agitation.

The following tests were carried out with sheep. A safety test was initiated in sheep 3787 on day 1. The sheep was inoculated subcutaneously (SC) with 6.0 ml of the vaccine without adjuvant. The sheep was autoinoculated with 10 ml of his own blood on the 5th, 6th, 7th and 8th days after initial inoculation. The rectal temperature of the sheep was determined twice daily throughout the test.

Heparinized blood, 15 samples, were taken during the 6-week observation; each sample was assayed for BTV in six embryonated chicken eggs. No observable antibodies to BTV was found during the 6-week period.

At six weeks after inoculation, the sheep was given an immunity challenge with virulent BTV serotype 11. A low-level (non-titrable) viremia was detected on days 7–11 after challenge. The temperature of the sheep was elevated on day 7 after challenge. The sheep had precipitin antibodies to BTV beginning on day 7 after challenge. Sera were not tested for neutralizing antibodies. The sheep was apparently partially protected by the 6.0 ml of candidate vaccine given subcutaneously without adjuvant for the safety test.

All remaining vaccine was given to four sheep on a second day 1 in an efficiacy test. Two sheep, 3795 and 3796, were each given SC 2 ml of vaccine emulsified in 2 ml of incomplete Freund's adjuvant (Difco). Two sheep, 3797 and 3798, were each given SC 2 ml of vaccine mixed with 2 ml of aluminum hydroxide.

Heparinized blood for viremia was collected on days after vaccination only if rectal temperatures were found to be elevated. All heparinized blood samples were inoculated into six embryonated chicken eggs and any dead embryos were subpassaged in BHK-21 cells three times. All eight samples collected after vaccination were negative. For this reason it was concluded that the elevated temperatures in sheeps 3795 and 3798 were due to intercurrent infections and were unrelated to the vaccine. The four sheep had precipitin antibody by 21 days after vaccination.

Immunity challenge was given six weeks after vaccination. The response to immunity challenge was excellent. Rectal temperatures did not reach 104° F. in any of the four sheep for the four-week observation period after challenge. The four sheep had detectable but non-titrable viremia between days 3 and 13 after challenge but for as little as 5 days in sheep 3796 and 3798, for 6 days in sheep 3797, and for 8 days in sheep 3795. The low-grade viremia was remarkable in two respects. In all 15 instances that viremia was detected, it was non-titrable and would therefore most likely not be transmissible by vector bite and the sheep remained clinically normal without elevated temperatures. All these results indicate excellent protection against the virus, without achieving the ultimate total absence of viremia.

It is obvious from the above results that the subject method provides for a highly effective vaccine. The method for inactivation of the virions is simple, requires no special equipment, and provides complete inactivation of the virions. The virion may then be used directly and is acceptable to the host and effective in providing for an effective immunogenic response. No significant detrimental effects are observed from the use of the virion and the vaccinated host obtained effective protection against infection from viral invasion and proliferation.

Although the foregoing invention has been described in some detail by way of illustration and example for purposes of clarity of understanding, it will be obvious that certain changes and modifications may be practiced within the scope of the appended claims.

What is claimed is:

1. A method for preparing a vaccine by inactivating a non-enveloped virus which comprises:

contacting said virus with an inactivating amount of a cis-diamine chelated platinous halide and a small but effective amount of a non-ionic detergent for a sufficient time to inactivate said virus and retain intact virion particles for preparing said vaccine.

2. A method according to claim 1, wherein said platinous halide is cis-diamine platinous chloride and said non-ionic detergent is a polyalkylene glycol, wherein said alkylene group is of from 2 to 3 carbon atoms.

3. A method according to claim 2, wherein said non-ionic detergent is combined with said virus prior to combining said platinous halide.

4. A method according to any of claims 1, 2 or 3, wherein said virus is a double stranded RNA virus.

5. A method according to claim 4, wherein said virus is an orbivirus.

6. A method according to claim 5, wherein said virus is a bluetongue virus.

7. A method for protecting a host from a viral infection which comprises:

administering to said host in an amount sufficient to produce an immunogenic response an inactivated virus according to any of claims 1, 2 or 3.

8. A method for protecting a host from a viral infection, which comprises:

administering to said host in an amount sufficient to produce an immunogenic response an inactivated virus according to claim 4.

9. A method according to claim 8, wherein said virus is bluetongue virus.

10. A vaccine comprising an inactivated virus prepared according to a method according to any of Claims 1, 2 or 3 in combination with an adjuvant.

11. A vaccine according to claim 10, wherein said adjuvant is aluminum hydroxide.

12. A vaccine according to claim 10, wherein said virus is an orbivirus.

13. A method for preparing a vaccine by inactivating a non-enveloped double-stranded RNA virus which comprises:

contacting said virus with an aqueous medium containing an inactivating amount of cis-diamine chelated platinous halide and from about 0.001 to 0.75 weight percent of a non-ionic detergent for a sufficient time to inactivate said virus and retain intact virion particles.

14. A method for protecting a host from a viral infection which comprises:

administering to said host in an amount sufficient to produce an immunogenic response an inactivated virus according to claim 13.

15. A vaccine comprising an inactivated virus prepared according to a method according to claim 13 in combination with an adjuvant.

16. A vaccine according to claim 15, wherein said adjuvant is aluminum hydroxide.

17. A vaccine according to claim 15, wherein said virus is an orbivirus.

* * * * *